US005776723A

United States Patent [19]

Herold et al.

[11] Patent Number: 5,776,723

[45] Date of Patent: Jul. 7, 1998

[54] RAPID DETECTION OF MYCOBACTERIUM TUBERCULOSIS

[76] Inventors: Christopher D. Herold, 205 12th St., Del Mar, Calif. 92014; Michael O'Hagan, 1160 Via Espana, La Jolla, Calif. 92037

[21] Appl. No.: 598,255

[22] Filed: Feb. 8, 1996

[51] Int. Cl.[6] .................... C12Q 1/04

[52] U.S. Cl. .................... 435/34; 435/29; 435/4

[58] Field of Search .................... 435/29, 32, 34, 435/240.3, 4, 7.2, 7.32, 863

[56] References Cited

PUBLICATIONS

Alugupalli et al., "Detection of 2–Eicosanol by Gas Chromatography–Mass Spectrometry in Sputa from Parients with pulmnary Mycobacterial Infections," J. Clin. Microbiol. 1993, 31, 1575–1578, Jun. 1993.

Dworzanski et al., "Pyrolytic Methylation–Gas Chromatography of Whole Bacterial Cells for Rapid Profiling of Cellular Fatty Acids," Appl. Environ. Microbiol. 1990, 56 1717–1724, Jun. 1990.

O'Hagan, "Aggregating Template or Rule Antecedents in Real–Time Expert Systems with Fuzzy Set Logic," Twenty–second Asilomar Conference on Signals, Systems and computers, Maple Press, 1988, 681–68, 1988.

J.M. Kirihara, et al. (1985) Improved detection times for *mycobacterium avium* complex and *mycobacterium tuberculosis* with the BACTEC radiometric system. J. Clin. Microbiol. 22(5):841–845.

M.A. Lambert, et al. (1986) Analysis of mycolic acid cleavage products and cellular fatty acids of mycobacterium species by capillary gas chromatography. J. Clin. Microbiol. 23(4):731–736.

M. O'Hagan (1988) Fuzzy decision aids. Twenty–first Asilomar Conference on Signals, Systems and Computers. Maple Press.

M. O'Hagan (1988) Aggregating template or rule antecedents in real–time expert systems with fuzzy set logic Twenty–second Asilomar Conference on Signals. Systems and Computers. Maple Press.

M. Otto, et al. (1988) Fuzzy inference structure for spectral library retrieval systems. IFSA 29–30.

G. Bortolan, et al. (1988) Classification of ECG signals—fuzzy pattern matching. IFSA 55–56.

A. Brisson–Noel, et al. (1989) Rapid diagnosis of tuberculosis by amplification of mycobacterium dna in clinical samples. Lancet 2:1069–1071.

B.A. Wolf, et al. (1990) Long–chain fatty alcohol quantitation in subfemtomole amounts by gas chromatography–negative ion chemical ionization mass spectrometry. J. Chromatography 509:325–332.

W. Pedrycz (1990) Fuzzy sets and neurocomputations foundations of pattern recognition. Tutorials of the International Conf. on Fuzzy Logic & Neural Networks 89–120.

B. Boddinghaus, et al. (1990) Detection and identification of mycobacteria by amplification of rRNA. J. Clin. Microbiol. 28(8):1751–1759.

S. Alugupalli, et al. (1992) Gas chromatography –mass spectrometry methods for analysis of secondary alcohols, present in the *Mycobacterium avium* complex. J. Microbiol. Meth. 15:299–240.

S. Alugupalli, et al. (1992) Secondary fatty alcohols of *Mycobacterium xenopi*. J. Gen. Microbiol. 138:2499–2502.

M. Fauville–Dufaux, et al. (1992) Rapid detection of tuberculous and non–tuberculous mycobacterium by polymerase chain reaction amplification of a 162 bp dna fragment from antigen 85. Eur. J. Clin. Microbiol. Infect. Dis. 11(9):797–803.

W. Pedrycz (1993) Fuzzy control and fuzzy systems. Second Extended Edition. John Wiley & Sons, Inc. New York, pp. 42–51.

S. Alugupalli, et al. (1993) Detection of 2–eicosanol by gas chromatography–mass spectrometry in sputa from patients with pulmonary mycobacterial infections. J. Clin. Microbiol. 31(6):1575–1578.

G.M.E. van der Vliet, et al. (1993) Nucleic acid sequence–based amplification (NASBA) for the identification of mycobacteria. J. Gen. Microbiol. 139:2423–2429.

Tuberculosis: pathogenesis, protection & control. (1995) B.R. Bloom, ed. ASM Press, Wash., DC, pp. 1–59.

B. Orsat, et al. (1996) Homocarbonates as substrates for the enantioselective enzymatic protection of amines. J. Am. Chem. Soc. 118:712–713.

J.T. Simpson, et al. (1990) Pentafluorobenzyl chloroformate as a derivatization reagent for NCI/MS. 43rd ASMS Conference on Mass Spectrometry and Allied Topics p. 472.

*Primary Examiner*—John Kight

*Assistant Examiner*—Dameron Jones

*Attorney, Agent, or Firm*—Knobbe, Martens, Olson & Bear, LLP

[57] ABSTRACT

A rapid, sensitive method for the detection of *M. tuberculosis*. A sample suspected of containing *M. tuberculosis* is extracted, derivatized and analyzed for the presence of two particular characterizing compounds specific to *M. tuberculosis*. One preferred analytical method involves a fuzzy matching process.

16 Claims, 6 Drawing Sheets

RAPID DETECTION OF MYCOBACTERIUM TUBERCULOSIS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all rights whatsoever.

FIELD OF THE INVENTION

The present invention relates to rapid detection of mycobacteria. More specifically, the invention relates to the detection of two characterizing compounds specific to *Mycobacterium tuberculosis*.

BACKGROUND OF THE INVENTION

Tuberculosis (TB), a chronic, recurrent infection most common in the lungs, is caused by several species of mycobacteria, the most common of which is *M. tuberculosis*. TB has reached global epidemic proportions with approximately one-third of the world's population infected and is the largest cause of death arising from a single pathogen. With global control of TB remaining at the 1990 level, it is estimated that 30 million people will die from TB in the last decade of the 20th century (*Tuberculosis: Pathogenesis, Protection and Control*, Snider et al., eds., ASM Press, Washington, D.C., 1995).

Methods for early detection of *M. tuberculosis* will ensure rapid isolation and treatment of infected patients which will help curb the spread of TB. Most current *M. tuberculosis* screening procedures take weeks for results to be observed, mainly due to the time required to culture the bacterium from sputum or other secretions.

One well-known screening procedure for *M. tuberculosis* infection is the purified protein derivative (PPD) test which entails injecting *M. tuberculosis* proteins under the skin. A positive reaction 2–3 days post-injection indicates cellular immunity to the bacterium. However, a positive result only indicates the presence of a mycobacterial infection, not the species of mycobacteria responsible for the infection.

Various biochemical mycobacterial isolation and identification methods have been used which may require a total time of six to eight weeks or more. More rapid identification techniques include radiometric testing, DNA probe techniques and high performance liquid chromatography (HPLC). One radiometric method, BACTEC (Becton-Dickinson, Sparks, Md.), uses a broth matrix, optimized for mycobacterial growth, which contains $^{14}$C-palmitic acid which is metabolized by mycobacteria to $^{14}Co_2$ which is expired and quantitated (Kirihara et al., *J. Clin. Microbiol.*, 22:841–845, 1985).

Radiometric and non-radiometric DNA probe methods involve hybridization of a labeled *M. tuberculosis* DNA probe complementary to a region of *M. tuberculosis* ribosomal RNA. Detection of the label confirms the presence of *M. tuberculosis*. Radiometric, DNA probe and HPLC-based methods are typically able to detect and identify mycobacteria in approximately two to three weeks which constitutes a clinically significant delay in determination of *M. tuberculosis* infection.

Further attempts to reduce detection and speciation time include the use of the polymerase chain reaction (PCR) directly on patient samples such as sputa and bronchial lavage washings (Fauville-Dufaux et al., *Eur. J. Clin. Microbiol. Infect. Dis.*, 11:797–803, 1992; Brisson-Noel et al., *Lancet*, 2:1069–1071) . Although this method is promising and very sensitive, it has two major limitations: false positive results caused by contamination with PCR products and false negatives caused by inhibitors of *Thermus aquaticus* (Tag) DNA polymerase.

Nucleic acid sequence based amplification (NASBA), an isothermal amplification technique involving amplification of 16S ribosomal RNA, has also been used in the identification of various mycobacteria species including *M. tuberculosis* (Boddinghaus et al., *J. Clin. Microbiol.*, 28:1751–1759, 1990; van der Vliet et al., *J. Gen. Microbiol.*, 139:2423–2429, 1993). Using a related concept, Gen-Probe (San Diego, Calif.) has developed a sensitive and specific assay for direct detection of *M. tuberculosis* from patient sputa, bronchial washings or bronchial alveolar lavage (BAL) in less than one day after receipt of the specimen.

Classification of mycobacteria by fatty acid profiles using gas chromatography (GC) and GC-mass spectrometry (GCMS) has also been performed. A number of fatty acids have been identified in an attempt to classify mycobacteria at the genus and species level. Some mycobacteria can be classified by the presence of a peak exclusive to their species, while others must be classified by groups of interrelating peaks. *M. tuberculosis* has been reported to contain a high concentration of hexacosanic acid (Lambert et al., *J. Clin. Microbiol.*, 23:731–736, 1986). Again, the major disadvantage of this method is the 2–3 week incubation time required prior to GC analysis.

The possibility of mycobacterial speciation based on fatty alcohol profiles has also been considered. Many of the fatty alcohols identified in mycobacteria have been found in *M. xenopi* (Alugupalli et al., *J. Gen. Microbiol.*, 138:2499–2502, 1992), including 2-octadecanol, 2-eicosanol and 2-docosanol. Alugapalli et al. (*J. Microbiol. Meth.*, 15:229–240, 1992) identified the presence of 2-octadecanol and 2-eicosanol in *M. avium* by GC-MS analysis. Larsson et al. (*J. Clin. Microbiol.*, 31:1575–1578, 1993) detected the fatty alcohol 2-eicosanol from sputum of patients infected with either *M. tuberculosis* or *M. avium* by GC-MS analysis.

Thus, there is a need for a rapid, simple, sensitive method for detection of *M. tuberculosis* which will ensure early detection and thus help prevent spread of the disease. The present invention satisfies this need.

SUMMARY OF THE INVENTION

One embodiment of the present invention is a method for detecting the presence of *M. tuberculosis* in a sample, comprising the step of analyzing the sample for the presence of either or both of two characterizing compounds having mass spectrometry values of m/e 484 and 486 and gas chromatography retention times relative to a $d_{37}$ octadecyl alcohol internal standard of about 1.022 and about 1.032, respectively, when derivatized with pentafluorobenzoyl chloride (PFBO). The method may further comprise the step of detecting 2-eicosanol in the sample, wherein the m/e 486 compound has a GC-MS peak having a first peak area, wherein the ratio of the first peak area to a second peak area comprising 2-eicosanol is greater than one. Preferably, the sample is sputum, alveolar washings or bronchial alveolar lavage. According to one aspect of this embodiment, the characterizing compounds are fatty alcohols. Advantageously, the method further comprises culturing the sample prior to the analyzing step. Preferably, the analyzing step is GC-MS or MS-MS.

The method may further comprise the steps of detecting a reference compound common to more than one species of mycobacteria and comparing the quantity of the reference compound to the quantity of the characterizing compound or compounds. In one aspect of this preferred embodiment, the reference compound is 2-eicosanol, and at least one of the characterizing compounds is of greater or comparable intensity to the reference compound if *M. tuberculosis* is present in the sample. Advantageously, the method further comprises obtaining and comparing GC-MS peaks for 2-eicosanol and the m/e 486 compound to determine the relative quantities thereof in the sample.

Another embodiment of the invention is a method of identifying a microorganism present in a sample, the method comprising the steps of analyzing the sample by GC-MS to obtain a first set of GC-MS ion species data; and comparing the first set of GC-MS ion species data to a panel of GC/MS ion species data by a fuzzy matching process to generate fuzzy match integral data vectors, wherein the panel of GC/MS ion species data comprises data from known species of microorganisms. The method may further comprise for at least one of the known species of microorganism, identifying a GCMS peak characteristic of the species and determining whether the characteristic peak is present in the sample. The method may also include the step of using an adjustable aggregation process simultaneously utilizing all of the ion species data to reduce the integral data vectors to aggregated scalar values using a vector dot product of a sorted list of the ion species data with ME-OWA weights generated by adjustment of a single optimism or confidence parameter for ordering and comparison in a speciation process. Preferably, the aggregation process is maximum entropy-ordered weighted averaging. Advantageously, the method further comprises the step of using an ARG MAX to choose a proper index among said aggregated scalar values. The method may also further comprise the step of using a threshold modified matching function to eliminate noise in the GC-MS ion species data. Preferably, the microorganism is a mycobacterium.

DETAILED DESCRIPTION OF THE PREFERRED EMBODIMENTS

Figure 1:
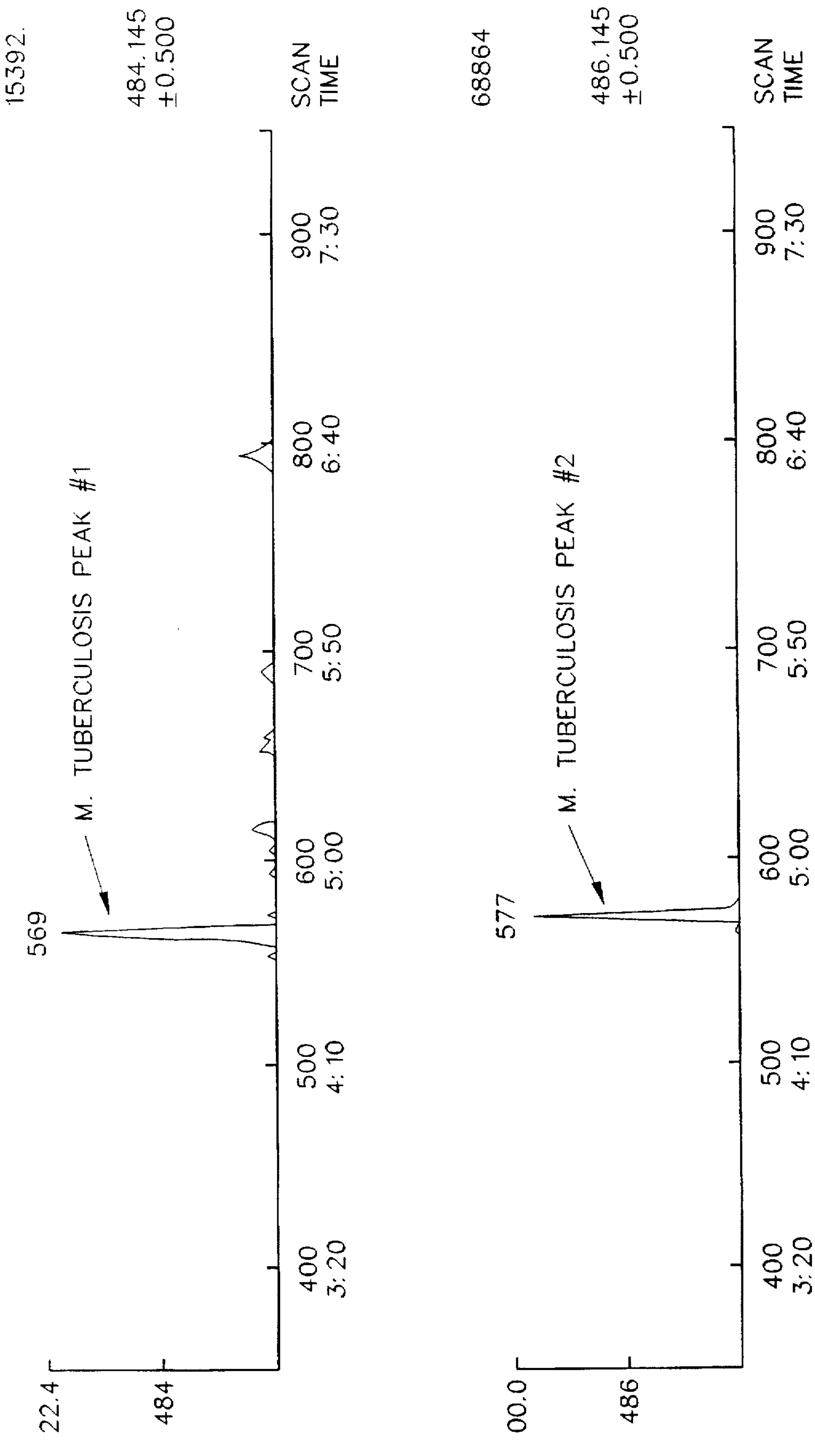
FIG. 1 illustrates selective ion monitoring of m/e 484 and 486 from a GC-MS chromatogram of *M. tuberculosis* PFBO derivatives. The GC retention time is shown on the x-axis and the peak intensity is shown on the y-axis.

The present invention discloses a rapid detection method for *M. tuberculosis* based on GC-MS detection of two characterizing compounds specific to *M. tuberculosis*. These two derivatives have characteristic molecular weights and GC retention times. This method allows rapid detection of *M. tuberculosis* in a patient's secretions, including sputa, bronchial washings or bronchial alveolar lavage. Although the definitive identification of each peak has not yet been determined, they appear to be multi-unsaturated fatty alcohols due to their derivatization by PFBO, mass to charge ratios and relative retention times.

The detection of underivatized (free) fatty alcohols, present in large quantities in a number of mycobacteria (i.e. 2-eicosanol in *M. avium*), is possible using analytical instruments such as GC-MS. Detection of other secondary alcohols, present in far lesser quantities, is near impossible without prior derivatization. To boost the sensitivity of fatty alcohol detection, GC-MS can be used in conjunction with the fatty alcohol derivatization procedure of Wolf et al. using PFBO (*J. Chromatography*, 509:325–332, 1990). The PFBO reaction produces a fluorinated aromatic ester with a large electron capturing cross section making it ideally suited for negative chemical ionization (NCI) GC-MS. The ionization process of NCI involves relatively low energy with no significant fragmentation of the derivatized alcohols, resulting in a simple mass spectrum consisting of a single ion species equal to the molecular weight of the derivatized alcohol.

Moreover, by reacting the alcohol with PFBO, the chromatographic characteristics of the alcohol are improved. The alcoholic hydrogen, which is replaced by the pentafluorobenzoyl group, is no longer available to form hydrogen bonds with active sites on the GC column, thus increasing resolution. The limit of detection reported by Wolf et al. (ibid.) when using NCI GC-MS was approximately 0.4 femtomole of fatty alcohol.

Although the use of PFBO as a derivatizing reagent is described herein, it is also contemplated that any derivatizing agent capable of reacting with fatty alcohols can also be used to identify the two peaks specific to *M. tuberculosis*. For example, the derivatizing agent pentafluorobenzyl chloroformate (Simpson et al., 43rd ASMS Conference on Mass Spectrometry and Allied Topics, p. 472) may be used with mass spectrometry-mass spectrometry (MS-MS) in which identification is based on specific, characteristic fragmentation patterns of a selected derivatized ion into daughter ions. The use of diallyl carbonate in conjunction with an esterase is also contemplated (Orsat et al., *J. Am. Chem. Soc.*, 118:712–713, 1996), as is the use of bis(pentafluorobenzyl) carbonate in conjunction with an esterase.

Of course, the resulting derivatives will have different molecular weights and different GC retention times relative to an internal standard compared to the PFBO derivatives. Moreover, any analytical technique capable of detecting the compounds in question can be used.

Various species of mycobacteria are cultured in vitro for 10–21 days, followed by saponification and extraction of the cultured mycobacteria. An internal standard ($d_{37}$-octadecyl alcohol) with a representative m/e of 501 by negative chemical ionization NCI GC-MS after derivatization with PFBO, is added to account for variations in the absolute retention times of eluting compounds (viewed as peaks on the GC-MS chromatogram). Retention times are standardized by expressing them relative to the elution time of this compound. It is also contemplated that multiple internal standards may be used. As chromatographic conditions change, the absolute retention times of the peaks will vary from run to run, but the relative retention time will be stable to within 2%. The resulting extract is then treated with the derivatizing agent PFBO which will react with the hydroxyl group of the fatty alcohols. After derivatization, the sample is analyzed by GC-MS taking approximately 15 minutes per sample. When *M. tuberculosis* is present, a peak at a mass to charge ratio at m/e 486 and relative retention time of about 1.032, relative to the internal standard peak ($d_{37}$-octadecyl alcohol) found at m/e 501, is consistently observed. A secondary peak with an m/e value of 484 and relative retention time of about 1.022 (also relative to $d_{37}$-octadecyl. alcohol) is also consistently observed, but at a lower intensity (FIG. 1). The presence of this peak is confirmatory, but not necessary, for the presence of *M. tuberculosis*. Corresponding peaks of similar intensity were not found in other mycobacteria tested including *M. avium, M. intracellular, M. smegmatis, M. xenopi, M. fortuitum, M. kansasii, M. gordonae* and *M. bovis*. In vitro, at 21 days growth in BBL 7H9 broth, the two peaks have been demonstrated to be of equal or greater intensity than the peak representative of 2-eicosanol found in *M. tuberculosis*.

To guard against the possibility that the m/e 484 and m/e 486 compounds may be detected as contaminants or minor peaks in mycobacterial species other than *M. tuberculosis*, in another preferred embodiment the integrated peak area of the m/e 486 peak is compared to that of 2-eicosanol which has an m/e value of 492. The ratio of these peak areas for *M. tuberculosis* is greater than one, preferably greater than about 5 or 10. In a particularly preferred embodiment, the ratio is greater than about 100. In a more particularly preferred embodiment, the ratio is greater than about 200.

Although GC-MS was used to detect the two fatty alcohol peaks specific to *M. tuberculosis*, the use of any detection technique sufficiently sensitive to detect either or both of these peaks is also within the scope of the invention. Such techniques include, for example, thin layer chromatography and HPLC.

The present method has been used for identification of *M. tuberculosis* from subcultured patient samples which have been allowed to grow for 10–21 days before analysis. However, with sensitive instrumentation, rapid identification of the two fatty alcohols characteristic for *M. tuberculosis* can be performed directly on patient samples, circumventing the culturing step, thereby allowing direct analysis. For direct analysis, the sample does not undergo any culturing steps. The sample is immediately saponified, extracted and derivatized. For a sample size of 50 (variable), preparation will take less than one working day. Analysis on the GC-MS using present methodologies is performed overnight with results available the next working day. Thus, the entire analytical process takes less than 24 hours, a significantly shorter period of time than is required for most other mycobacterial detection techniques.

The spectral data obtained by GC-MS may also be directed into a computer processor containing GC-MS sample data from a number of mycobacterial species which will match the sample species to one of the stored reference sample chromatograms within 15 minutes. One such processor is a "fuzzy matching processor" which can be used in a "fuzzy matching process" as described below.

Figure 2:
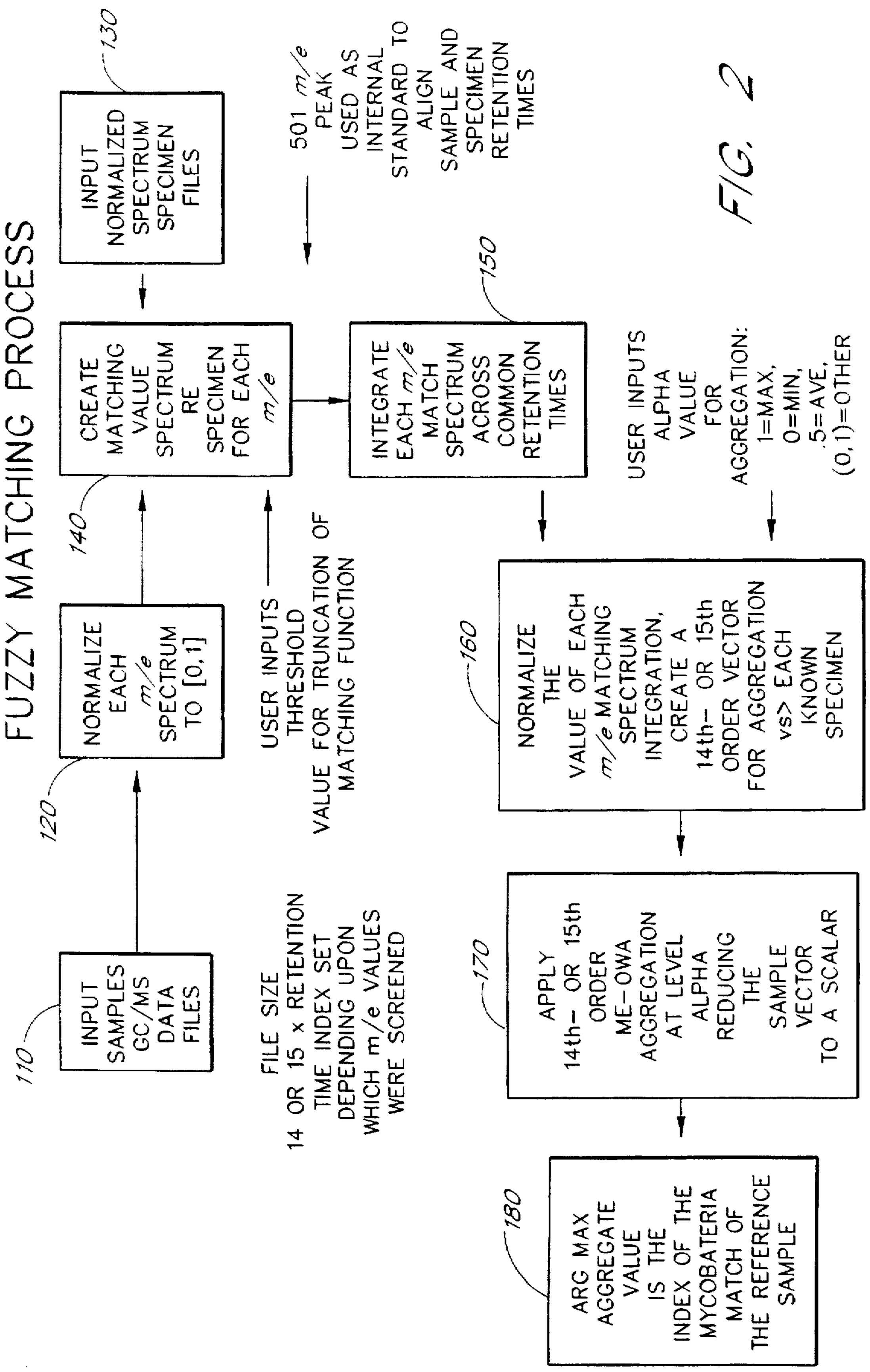
FIG. 2 is a flow diagram illustrating the fuzzy matching process for identifying species of mycobacteria present in a sample.

The fuzzy matching process is illustrated in FIG. 2. Computer files of ASCII data are normally available from GC-MS apparatus. The explanation of the algorithm will use GC-MS runs from fatty alcohols contained in mycobacterial samples. These fatty alcohols are less abundant, but possibly more species-specific, than fatty acids.

The order of the GC-MS data generated for each ion species is typically 583 points gathered in about 5 minutes of analysis. The spectrum for each ion species is obtained in parallel with one temperature sweep of the GC-MS. Referring to FIG. 2, in step 110 of process 100, each spectrum so obtained is first normalized by dividing each entry in the spectrum by the MAX count obtained over the entire set of 583 values. This operation is performed over all ion species spectra, which for the fatty alcohol derivatives range from m/e values of 408 or 422 to 548. This results in 14 or 15 separate spectra, normalized to the fuzzy range of (0,1) (Step 120). Having previously performed the same normalization on a series of known mycobacteria GC-MS spectra, again with a common m/e internal standard (Step 130), a fuzzy match can be performed using a thresholded version of a fuzzy matching function developed by Pedrycz (*Pattern Recognition Lett.*, 5:305–314, 1989) (Step 140). This matching function, which compares two fuzzy numbers returning a single fuzzy match value, has a simple and easily calculated form:

$$
\begin{aligned}
\text{FUZZY\_MATCH}(a,b) &= 0.5[a/b+(1-b)/(1-a)] && \text{if } a<b,\\
&= 1 && \text{if } a=b\\
&= 0.5[b/a+(1-a)/(1-b)] && \text{if } b<a\\
&= 0 && \text{if either a or b} = 0
\end{aligned}
$$

Figure 3:
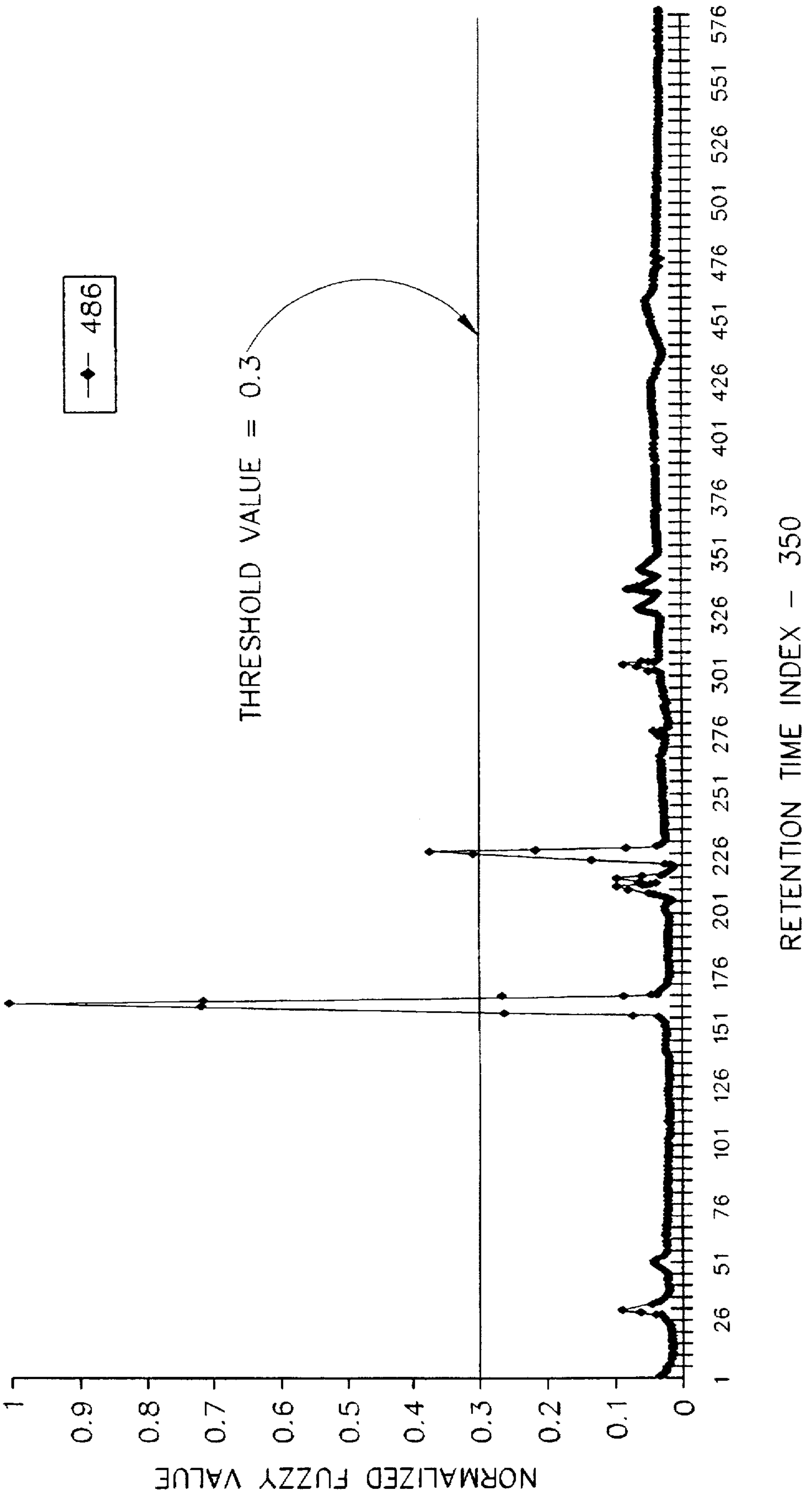
FIG. 3 is a fuzzy match spectrum for the m/e 486 compound (Sample 13*b*) showing the threshold value and the noisy spectral data below the threshold value. The retention time index is shown on the x-axis and the normalized fuzzy value is shown the y-axis.

Our fuzzy speciation algorithm uses a truncated version of the FUZZY_MATCH(a,b,THRESHOLD), which returns to a value of 0 when either a or b is less than a THRESHOLD VALUE in (0,1). For the runs calculated in the current study, THRESHOLD is arbitrarily set to 0.3. The threshold concentrates attention of the matching process on significant peaks and ignores noisy spectral floor values. This THRESHOLD VALUE is shown in FIG. 3 for the m/e 486 compound **13*b***.

The fuzzy matching function with a threshold is applied on an element-by-element basis to the corresponding retention time index values of the reference specimen and the unknown sample with the alignment offset calculated by the use of the internal standard peak spectral value. This produces a fuzzy match "spectrum" which can be integrated to obtain an overall fuzzy match figure of merit for this particular ion species relative to the known specimen for this particular ion species (Step 150). In the actual calculation some additional retention time jittering is performed as a function of the distance of a particular retention time index from the m/e 501 reference peak.

In an alternative embodiment, rather than feeding the data from Step 140 into Step 150, the data may be fed into a neural net pattern recognizer. One particularly preferred neural net pattern recognizer is the holographic neural technology (H-NeT) discovery package version 1.3 for windows (And America, Ltd., Oakville, Ontario, Canada).

Figure 4:
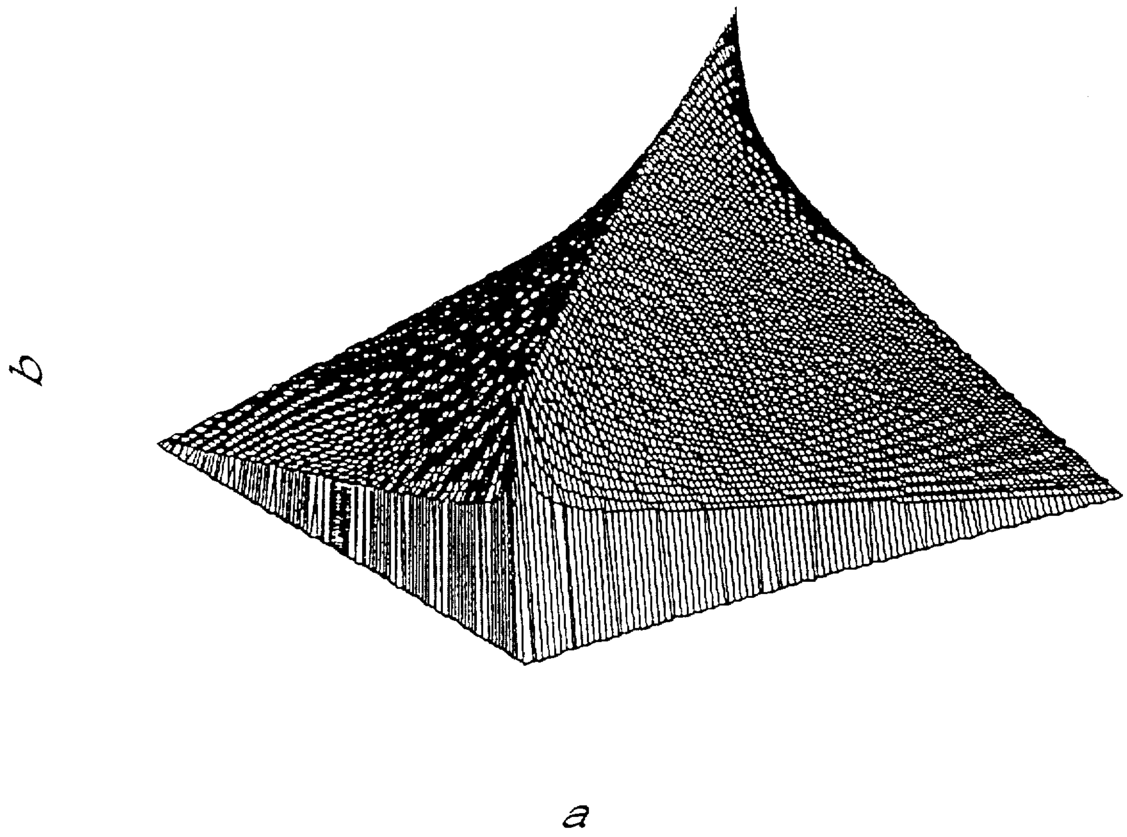
FIG. 4 is a graph showing a fuzzy matching function with threshold=0.0.

Because of possible slow time constant changes in the GC-MS apparatus, samples run at one time may not agree exactly in retention time alignment with themselves when run at a different time. To allow for this possible drift, retention time indices are assumed to float by at most ±2% as a function of their distance from the m/e 501 peak index value. That is, within ±50 retention index values of the IS peak, the alignment is assumed to be perfect as given by the offset of m/e 501 peak value to m/e 501 peak value. Within ±50–100 retention times, the matching indices are assumed to have a possible jitter of ±1 index value, etc. We calculate all the possible jittered match values and keep the MAX. The fizzy matching function with Threshold value=0.0 is shown in FIG. 4 and indicates how the match values take on a discrete "roof peak" appearance, while the values which do not match fall off precipitously in either direction from the peak.

The jittering of retention time indices varies as a function of the distance from the internal standard (IS) peak index. Within ±50 of IS peak index, the matching indices correspond after the correction for the internal standard offset. These offset values are shown for ten data samples in the "501index.h" file in Appendix B.

```
j + (IS peak index for sample - IS peak index for
specimen) = k
MATCH VALUE(k) = FUZZY_MATCH(VALUE(k),
VALUE(j),THRESHOLD)
```

Within ±100 of IS peak index, but >±50, the search is made for ±1 indices from j & k in both directions, since jitter in the indices could occur in either the sample or the specimen. This implies that a total of six paired comparisons is made for each j and k value. The MAX of the fuzzy match values is returned.

Within ±150 of IS peak index, but >±100, the search must be made for ±2 indices from j & k in both directions, since jitter in the indices could occur in either the sample or the specimen. This implies that a total of 10 paired comparisons is made for each j & k value. The MAX of the fuzzy match values is returned.

In the actual calculation, the retention time index used in the fuzzy matching is the retention time index from the GC-MS minus 350. The offset alignment based on the m/e 501 peak is applied before matching calculations begin. As noted above, a typical data set has 583 values. Padding with zero values allows the calculation to continue to the sample end points. The actual number of valid match points equals 583–offset value. The resulting fuzzy "MAX matching spectrum" is then integrated over all valid matching retention time indices (583–OFFSET) in number. The resulting scalar value is an un-normalized fuzzy value estimating the degree of match between the given specimen and the unknown sample for a given ion species (m/e value). For a given sample, the same matching and integration are performed across all of a limited set of ion species, typically 14 or 15 in number ranging from an m/e value of 408 or 422 to 548. This creates a matching integral data vector of order 14 or 15 to be compared with other matching vectors from matches with different known reference specimens.

Before making the comparison, the fuzzy values within the GC-MS data vector are normalized (Step 160) and an adjustable aggregation process is employed to reduce the integral data vectors to aggregated scalar values by vector dot product of a sorted list of the ion species data with ME-OWA weights generated by adjustment of a single optimism or confidence parameter for ordering and comparison in a speciation process. The aggregation process employed is ME-OWA (Maximum Entropy-Ordered Weighted Averaging) first formulated by O'Hagan (Proceedings of the 21st Asilomar Conference on Signals, Systems and Computers, Pacific Grove, Calif., November 1987) and solved for by O'Hagan (*Aggregating Template or Rule Antecedents in Real-Time Expert Systems with Fuzzy Set Logic*, Proceedings of the 22nd Annual Asilomar Conference of Signals, Systems and Computers, IEEE and Maple Press, 2:681–689, 1988, Pacific Grove, Calif.) (Step 170).

There is some arbitrariness in the choice of normalizing factors used to normalize the fuzzy integral match value in Step 160. One route is to first obtain the corresponding integral values for matches made between the specimen and itself and the sample itself. Some combination of these two self-matching values can be used as a divisor to normalize the fuzzy matching value for the unknown sample and the known specimen across the complete set of ion species. Two possible normalizing functions are:

```
MAX(SQRT(MATCH_INTEGRAL(SPECIMEN,SPECIMEN),
MATCH_INTEGRAL(UNKNOWN,UNKNOWN)) or
SUM(MATCH_INTEGRAL(SPECIMEN,SPECIMEN),MATCH_
INTEGRAL (UNKNOWN, UNKNOWN))
```

Figure 5:
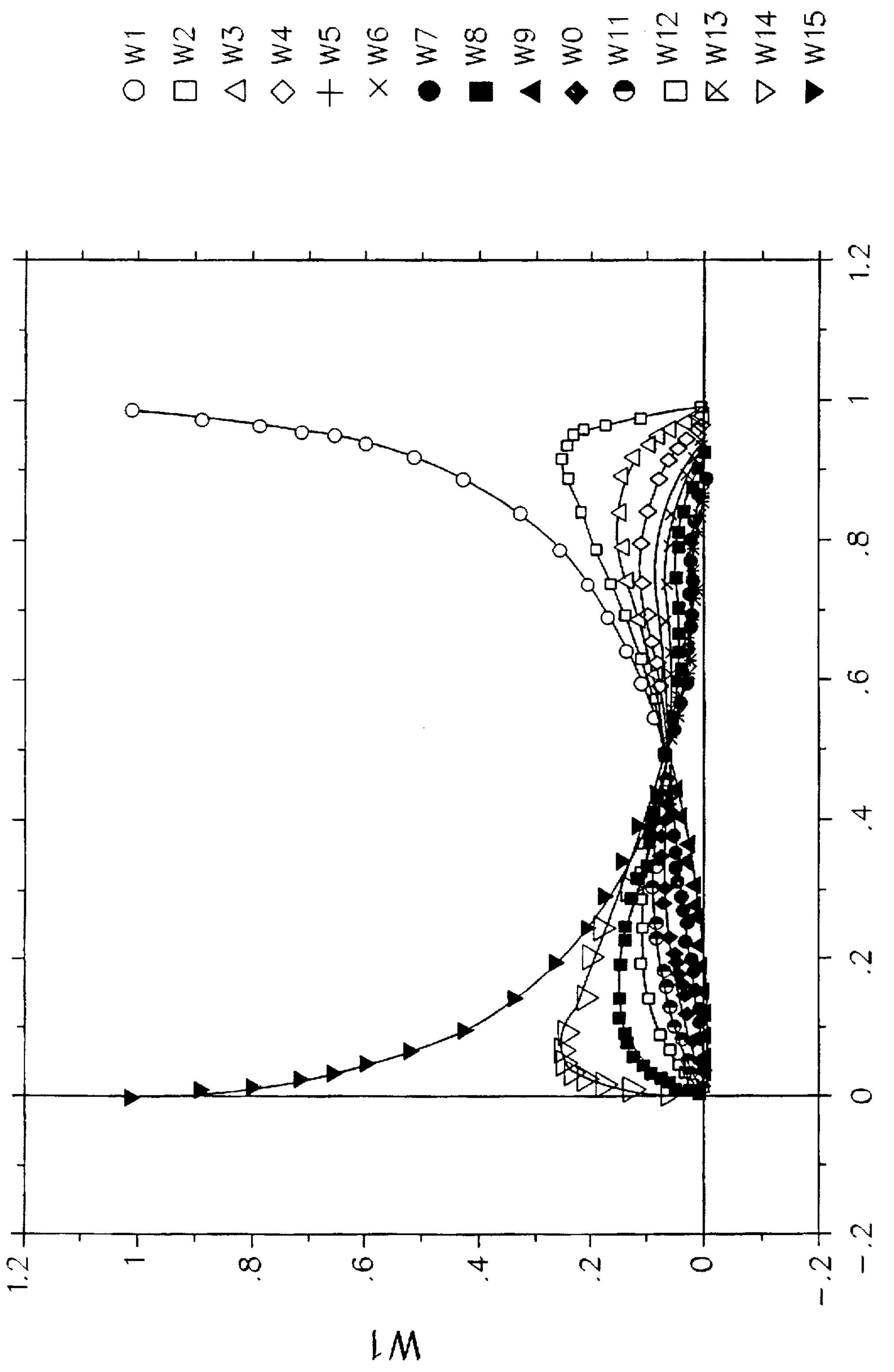
FIG. 5 is a graph showing the ME-OWA weights as a function of the confidence factor. The "W" values are defined in Appendix A. CF values are shown on the x-axis and W1 values are shown on the y-axis.

The latter expression is preferred for the current application. To perform this reduction, ME-OWA aggregation operators are used with an appropriate confidence factor set by the operator to allow optimism to range between max (1) and min (0). An optimism value of 0.5 will just produce an averaging of the vector components. The general behavior of the ME-OWA weights as a function of a single "confidence factor" parameter is shown in FIG. 5.

Figure 6:
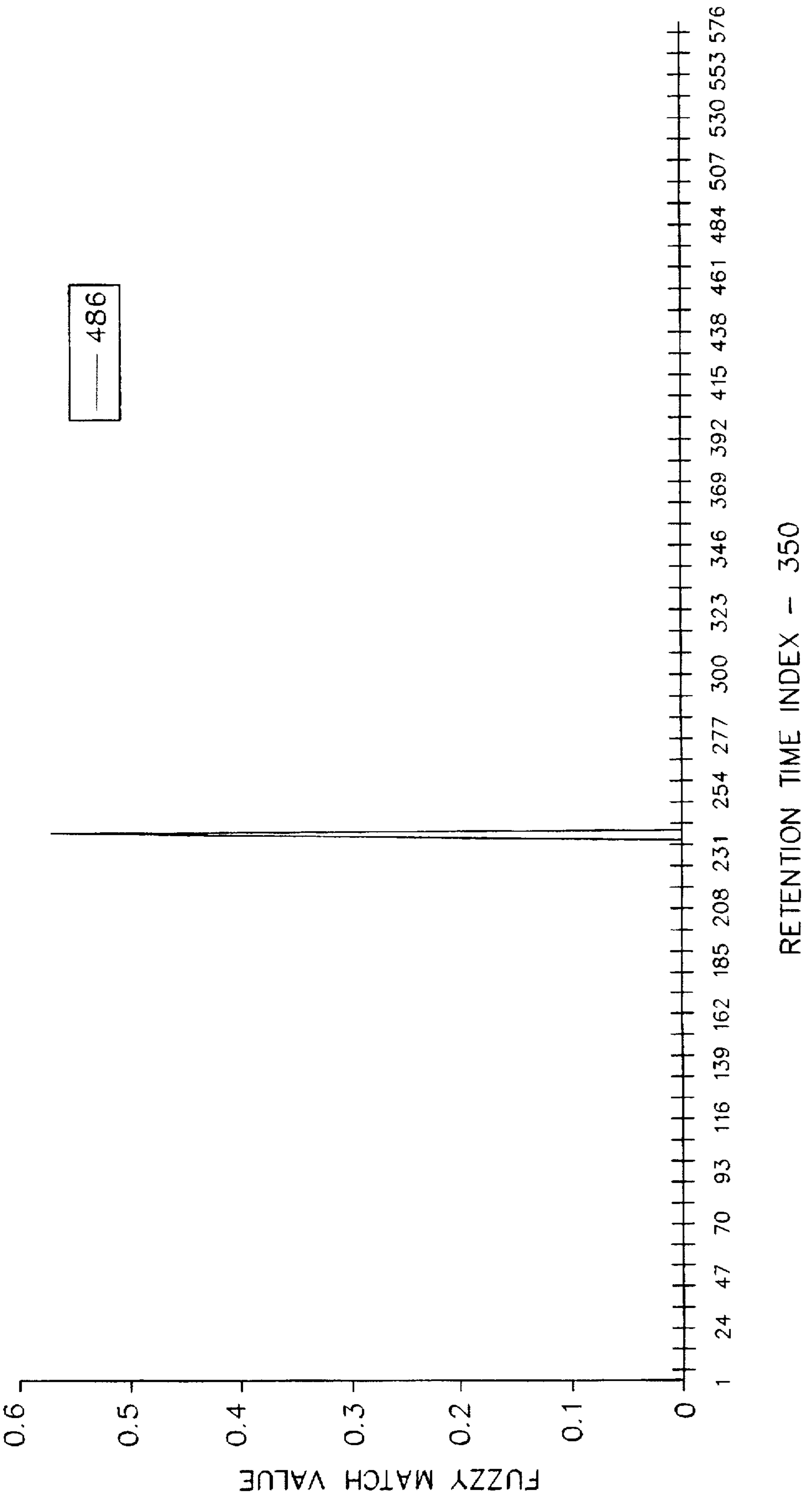
FIG. 6 is a graph showing a typical fuzzy match result for the m/e 486 compound, in this case between unknown sample 13*b* and specimen 17*b*, a known *M. tuberculosis* exemplar. The noise reduction is evident due to thresholding of the matching process at 0.3.

The reduction process is performed as follows. The match integral values developed for each ion species are normalized and sorted in descending order. Next, with the optimism or confidence value set at a fixed value, the ME-OWA weights are generated using polynomial fits for the appropriate order (14 or 15), depending upon MIN of the number of ion species that are present in the unknown or the specimen sample. A dot product of the ME-OWA weights thus obtained is performed with the match integral values (now sorted) with W1×largest, W2×next largest, etc. This operation may be viewed as a mathematical expectation operation with the ME-OWA weights playing the role of a discrete probability distribution. The same weights are applied to each specimen comparison vector and the ARG MAX, the specimen index showing the best match, is chosen (Step 180). A typical fuzzy match for the m/e 486 compound in *M. tuberculosis* is shown in FIG. 6.

As an example of the polynomial expressions for generating the ME-OWA aggregation weights, the 15th order set is shown in Appendix A. The ME-OWA weights can be plotted as a function of the Optimism (x), as in the polynomials shown in Appendix A, or confidence factor (CF) as shown in FIG. 5 for a 15th order set. For CF=0.5, the average, (1/15th), is the value for all the weights.

One preferred source code for the fuzzy matching process is shown in Appendix B. This source code applies to Steps 140 and 150 of FIG. 2. It will be appreciated by a person of ordinary skill in the computer software art that many variations of this source code may be used to produce equivalent results. The software program may be implemented using a standard personal computer with an 80×86 processor and a standard C-compiler.

Although the identification of mycobacteria by the fuzzy matching process has been described herein, the identification of any microorganism using this process is within the scope of the present invention if the sample microorganism contains a detectable characterizing compound. Nonlimiting examples of such microorganisms include bacteria (i.e. Streptococcus, Staphylococcus, Pseudomonas), viruses, yeast, protozoa, fungi and the like. It is also contemplated that mammalian cell samples may be analyzed using this method.

The entire process, from placing sputum sample into culture medium to obtaining positive *M. tuberculosis* results, is less than nine hours.

Example 1

Preparation of mycobacterial samples for GC-MS analysis

The following mycobacteria were grown for 10–21 days in 5 ml BBL 7H9 broth containing glycerol: *M. tuberculosis, M. avium, M. intracellular, M. smegmatis, M. xenopi, M. fortuitum, M. kansasii, M. gordonae* and *M. bovis*. Ten µl $d_{37}$-octadecanol was added to each sample as internal standard (m/e 501 internal standard), followed by addition of 2 ml 5% NaOH in 1:1 methanol:water. The samples were then incubated at 70° C. for 30 minutes, resulting in saponification of the sample. Two ml hexane was added and the samples vortexed vigorously for five minutes. The samples were centrifuged at 2,000 rpm for 10 minutes to eliminate emulsions, followed by removal of hexane and transfer to a clean 15 ml round bottom glass tube. The hexane was evaporated to dryness under ultrapure nitrogen. The remaining residue containing fatty alcohols was derivatized with PFBO by addition of 50 µl pyridine and 50 µl of a 10% solution of PFBO in acetonitrile. The samples were allowed to stand at room temperature and reaction was instantaneous. Two ml distilled water and two ml hexane were added to each sample. The samples were vortexed vigorously for 5 minutes to remove any unreacted PFBO. Samples were centrifuged if needed to remove emulsions. The hexane layer was removed and evaporated to dryness under nitrogen. The residue, which contained the derivatized fatty alcohols, was reconstituted with 100 µl acetonitrile (final extract) and subjected to GC-MS analysis as described in the following example.

Example 2

GC-MS analysis

One µl final extract produced according to Example 1 was injected, either manually or using an autosampler, in a Finnigan MAT 4500 Series GC-MS (Finnigan Corp., Palo Alto, Calif.) containing a 15 m×0.32 mm internal diameter column cross-linked with dimethylpolysiloxane (DB-1) with a 0.25 µm film thickness (Supelco, Bellafonte, Pa.). The GC-MS was operated in negative chemical ionization (NCI) mode monitoring ions at m/e 422, 436, 450, 464, 478, 484, 486, 488, 492, 501, 506, 520, 534 and 548 with a dwell time of 0.02 seconds per m/e. Split injection was used with the oven temperature program starting at 160° C., holding for 1 minute and ramping to 280 at 20° C./min. Injector and transfer line temperature were held at 280° C.; ionizer temperature was 100° C.; ionizer pressure was 0.75 torr; high vacuum was 1.5E–5torr with a manifold temperature of 110° C. Ultra high purity grade helium (Lab Specialty Gases, Inc., San Diego, Calif.) was used as the carrier gas at a rate of 1 ml/min.

The GC-MS results indicated that the ions produced having m/e values of 484 and 486 and GC retention times of 1.022 and 1.032 relative to the m/e 501 internal standard, respectively, were only present in samples of *M. tuberculosis* and not in any of the other mycobacteria tested.

Example 3

Rapid identification of *M. tuberculosis* in sputa

Sputa obtained from patients suspected of harboring a mycobacterial infection are saponified, extracted and derivatized without culturing in processing for GC-MS analysis as described in Example 1. The extract is then subjected to GC-MS analysis using the parameters described in Example 2. Peaks occurring at m/e values of 484 and/or 486 at relative retention times of about 1.022 and 1.032, respectively, to the internal standard ($d_{37}$-octadecyl alcohol) indicate the presence of *M. tuberculosis*.

While particular embodiments of the invention have been described in detail, it will be apparent to those skilled in the art that these embodiments are exemplary rather than limiting, and the true scope of the invention is that defined in the following claims.

APPENDIX A

APPENDIX A $$W1(x) = -.006 + .537 \cdot x - 13.64 \cdot x^2 + 144.771 \cdot x^3 - 783.987 \cdot x^4 + 2427.55 \cdot x^5 - 4450.642 \cdot x^6 + 4775.848 \cdot x^7 - 2770.914 \cdot x^8 + 671.477 \cdot x^9$$

$$W2(x) = .012 - 1.066 \cdot x + 26.746 \cdot x^2 - 282.454 \cdot x^3 + 1544.475 \cdot x^4 - 4777.171 \cdot x^5 + 8702.409 \cdot x^6 - 9247.094 \cdot x^7 + 5299.027 \cdot x^8 - 1264.87 \cdot x^9$$

$$W3(x) = -.001 + .144 \cdot x - 4.484 \cdot x^2 + 51.323 \cdot x^3 - 272.357 \cdot x^4 + 810.794 \cdot x^5 - 1414.245 \cdot x^6 + 1428.76 \cdot x^7 - 771.166 \cdot x^8 + 171.226 \cdot x^9$$

$$W4(x) = -.001 + .16 \cdot x - 5.18 \cdot x^2 + 62.329 \cdot x^3 - 344.289 \cdot x^4 + 1062.738 \cdot x^5 - 1927.158 \cdot x^6 + 2034 \cdot x^7 - 1154.524 \cdot x^8 + 271.923 \cdot x^9$$

$$W5(x) = -4.022E-4 + .076 \cdot x - 2.747 \cdot x^2 + 37.121 \cdot x^3 - 206.916 \cdot x^4 + 636.588 \cdot x^5 - 1154.527 \cdot x^6 + 1225.019 \cdot x^7 - 702.439 \cdot x^8 + 167.824 \cdot x^9$$

$$W6(x) = 1.856E-5 + .006 \cdot x - .672 \cdot x^2 + 16.941 \cdot x^3 - 99.914 \cdot x^4 + 304.053 \cdot x^5 - 541.641 \cdot x^6 + 567.707 \cdot x^7 - 324.318 \cdot x^8 + 77.838 \cdot x^9$$

$$W7(x) = 3.135E-4 - .05 \cdot x + 1.016 \cdot x^2 + 2.966 \cdot x^3 - 34.945 \cdot x^4 + 115.711 \cdot x^5 - 204.077 \cdot x^6 + 207.428 \cdot x^7 - 115.413 \cdot x^8 + 27.364 \cdot x^9$$

$$W8(x) = .001 - .104 \cdot x + 2.94 \cdot x^2 - 11.52 \cdot x^3 + 21.948 \cdot x^4 - 23.805 \cdot x^5 + 15.234 \cdot x^6 - 6.257 \cdot x^7 + 1.564 \cdot x^8$$

$$W9(x) = .001 - .163 \cdot x + 5.735 \cdot x^2 - 34.207 \cdot x^3 + 111.43 \cdot x^4 - 232.019 \cdot x^5 + 314.964 \cdot x^6 - 269.243 \cdot x^7 + 130.867 \cdot x^8 - 27.364 \cdot x^9$$

$$W10(x) = .001 - .2 \cdot x + 9.709 \cdot x2 - 71.354 \cdot x3 + 270.849 \cdot x4 - 621.872 \cdot x5 + 889.82 \cdot x6 - 775.341 \cdot x7 + 376.227 \cdot x8 - 77.838 \cdot x9$$

$$W11(x) = -4.257E-4 - .099 \cdot x + 13.871 \cdot x2 - 121.093 \cdot x3 + 508.863 \cdot x4 - 1244.039 \cdot x5 + 1849.507 \cdot x6 - 1647.159 \cdot x7 + 807.974 \cdot x8 - 167.824 \cdot x9$$

$$W12(x) = -.003 + .518 \cdot x + 12.628 \cdot x2 - 147.57 \cdot x3 + 697.644 \cdot x4 - 1822.748 \cdot x5 + 2825.709 \cdot x6 - 2587.041 \cdot x7 + 1292.785 \cdot x8 - 271.923 \cdot x9$$

$$W13(x) = -.007 + 2.768 \cdot x - 14.984 \cdot x2 + 10.855 \cdot x3 + 167.297 \cdot x4 - 718.382 \cdot x5 + 1377.365 \cdot x6 - 1423.551 \cdot x7 + 769.864 \cdot x8 - 171.226 \cdot x9$$

$$W14(x) = .015 + 9.644 \cdot x - 138.92 \cdot x2 + 957.536 \cdot x3 - 3768.813 \cdot x4 + 8983.061 \cdot x5 - 13177.916 \cdot x6 + 11621.223 \cdot x7 - 5647.504 \cdot x8 + 1161.678 \cdot x9$$

$$W15(x) = .994 - 12.404 \cdot x + 112.029 \cdot x2 - 647.86 \cdot x3 + 2327.815 \cdot x4 - 5253.386 \cdot x5 + 7436.538 \cdot x6 - 6397.848 \cdot x7 + 3054.085 \cdot x8 - 619.965 \cdot x9$$

APPENDIX B

FUZZ_COM.C

```
#include <stdlib.h>
#include <malloc.h>
#include <sys\types.h>
#include <stdio.h>
#include <math.h>
#include <string.h>
#include <assert.h>
#include "501index.h"
#define PEAKS 700
/****************************************************************

Routine to do a fuzzy compare of two vectors.  The vectors are expected
to each be in a different file, in ascii, one floating point number per
 line.  There is an arbitrary maximum of 600 lines allowed for in the
 program.  Both vectors ideally will be the same link. In the initial
 version of the program, provision is made for unequal length vectors.

Version 2: The include file 501index.h has been added.  It contains the
 scan # for the peak of the 501 internal standard (IS). The two vectors
 are lagged/advanced to line up these peaks.

The program calls fuzz_comp for each pair of values, and makes
a result vector, which is the running integral value of the comparison.
At the end of processing the comparison vector will be written to
another ascii file for future plotting by Excel.

****************************************************************/

extern double fuzz_comp(double a, double b);
long indices[12] =
    {
        1,2,3,4,5,6,7,8,9,10,11,12
    };
double pk1[PEAKS],pk2[PEAKS],result[PEAKS];
double cumdindex[PEAKS],cumresult[PEAKS],maximum,temp;
double sum;

void
main(int argc,char *argv[])
{
    FILE *in1,*in2,*out;/*user supplies names*/
    int npeaks,npeaks2,idx1,idx2,idx3,i,j;
    int run1,run2,pindex1,pindex2,offset,lim1,lim2,lim3,lim4;
    int length,start,current;
    int idx2max,idx2min,left_index,right_index;
    char msg[64];
    if(argc != 4)
    {
        fprintf(stderr,"fuzz requires 3 files:\n");
        fprintf(stderr,".....input file 1\n");
        fprintf(stderr,".....input file 2\n");
        fprintf(stderr,"and an appropriately named output file.\n");
        exit(0);
    }
    in1 = fopen(argv[1],"rt");
    if(in1 == NULL)
    {
        perror("Can't open in1 "); exit(-1);
    }
    in2 = fopen(argv[2],"rt");
```

FUZZ_COM.C

```
if(in1 == NULL)
{
    perror("Can't open in2 "); exit(-1);
}
out = fopen(argv[3],"wt");
if(out == NULL)
{
    perror("Can't open out "); exit(-2);
}
i = sscanf(argv[1],"%2d",&run1);
fprintf(stdout,"run1 = %d\n",run1);
i = sscanf(argv[2],"%2d",&run2);
fprintf(stdout,"run2 = %d\n",run2);
for(idx1 = 0; idx1 < NumEntries; idx1++)
{
    if(entry[idx1].run == run1)
        pindex1 = entry[idx1].index;
    if(entry[idx1].run == run2)
        pindex2 = entry[idx1].index;
}
fprintf(stdout,"pindex1 = %d\n",pindex1);
fprintf(stdout,"pindex2 = %d\n",pindex2);
/* clear the pk arrays first */
for(idx1 = 0; idx1 < PEAKS; idx1++)
    pk1[idx1] = pk2[idx1] = 0.0;
offset = (pindex1 - pindex2);
if (pindex1 < pindex2)
    start = 7 + abs(offset);
else
    start = 7;
/* read the stuff from in1 first, see how many there are*/
npeaks = 0;
for(idx1 = start; idx1 < PEAKS; idx1++)
{
    i = fscanf(in1,"%lf",&pk1[idx1]);
    if(feof(in1))break;/* don't count this time; no peak*/
    if(i != 1)/* scanf error */
    {
        sprintf(msg,"Fscanf error on in1 at %d\n",idx1);
        perror(msg);
        exit(-2);
    }
    npeaks++;
}
npeaks2 = 0;
if(pindex2 < pindex1)
    start = 7 + abs(offset);
else
    start = 7;
for(idx1 = start; idx1 < PEAKS; idx1++)/* read the second file */
{
    i = fscanf(in2,"%lf",&pk2[idx1]);
    if(feof(in2))break;
    if(i != 1)
    {
        sprintf(msg,"Fscanf error on in2 at %d ",idx1);
        perror(msg);
        exit(-2);
    }
    npeaks2++;
}
fprintf(stderr,"Npeaks  = %d\n",npeaks);
```

FUZZ_COM.C

```
fprintf(stderr,"Npeaks2 = %d\n",npeaks2);
/*
 * Now the two arrays are zero padded so that the offset
 * is taken into account and they are both lined up.  This
 * means that we can use the same index for both.  We will
 * start with the smaller of pindex1,pindex2.
 */
start = min(pindex1,pindex2);
lim1 = (start)/50;/*no of chunks to the left */
lim2 = (max(npeaks,npeaks2)-start);
/*lim2 = max(npeaks,npeaks2);       */
lim3 = lim2%50;/* no of orphan values on right */
lim2 /= 50;/* no of right chunks */
fprintf(stderr,"No. of right chunks = %d\n",lim2);
lim4 = start%50;/*orphans on left*/
start += 7;/*arrays are padded on left with 7 zeros */
left_index = start - (lim1 * 50);
right_index = start + (lim2*50);
idx2max = -1; idx2min = 100;
/*
 * We want to use start as a fiducial mark in the center of the two
 * arrays.  The outer loops will count chunks, moving down to the left
 * and up to the right.  Inner loops counting 50 will be used, the number
 * of values to be considered will be drawn from the indices array,
 * indexed by the chunk counter (outer loop).  A subroutine will invoke
 * the fuzzy comparison.
 */
/*
 * do the simple case, the left chunks of 50, to begin.
 */
for(idx1 = 0;idx1 < lim1; idx1++)
{
/* idx1 * 50 is the left offset for the inner loop*/
    for(idx2 = start-(idx1*50);idx2 > (start -((idx1+1)*50));idx2--)
    {
    /*this should start with idx2 going from start to start-50*/
        if(idx2 > idx2max)idx2max = idx2;
        if(idx2 < idx2min)idx2min = idx2;
        if(!idx1)
        {/* at center only look at one */
            result[idx2-7] = fuzz_comp(pk1[idx2],pk2[idx2]);
        }
        else
        {
            maximum = 0.0;
            for(idx3=idx2-indices[idx1-1];idx3 < idx2+indices[idx1-1] ;idx3++)
            {
                if(idx3 >= 0 && idx2 >= 0)
                {
                    temp = fuzz_comp(pk1[idx3],pk2[idx2]);
                    if (maximum < temp)maximum = temp;
                        temp = fuzz_comp(pk1[idx2],pk2[idx3]);
                    if(maximum < temp)maximum = temp;
                }
            }
        result[idx2-7] = maximum;
        }
    }/* for idx2 */
}/* for idx1*/
fprintf(stderr,"Finished left side, proceeding to right.\n");
for(idx1=0; idx1 < lim2; idx1++)
{
```

FUZZ_COM.C

```
    for(idx2 = start+(idx1*50);idx2< (start+((idx1+1)*50));idx2++)
    {
        if(idx2max < idx2)idx2max = idx2;
        if(idx2min > idx2)idx2min = idx2;
        if(!idx1)
        {
        result[idx2-7] = fuzz_comp(pk1[idx2],pk2[idx2]);
        }
        else
        {
            maximum = 0.0;
            for(idx3=idx2-indices[idx1-1];idx3 < idx2+indices[idx1-1] ;idx3++)
            {
                if(idx3 >= 0 && idx2 >= 0)
                {
                    temp = fuzz_comp(pk1[idx3],pk2[idx2]);
                    if (maximum < temp)maximum = temp;
                    temp = fuzz_comp(pk1[idx2],pk2[idx3]);
                    if(maximum < temp)maximum = temp;
                }
            }
            result[idx2-7] = maximum;
        }

    }/*for idx2*/

}/* for idx1 */

fprintf(stderr,"idx2max + %d\n",idx2max);
fprintf(stderr,"idx2min = %d\n",idx2min);
for(idx1 = left_index; idx1 > 7; idx1--);
{
    maximum = 0.0;
    for(idx2 =idx1-(indices[lim1]);idx2 < idx1+indices[lim1];idx2++)
    {
        temp = fuzz_comp(pk1[idx1],pk2[idx2]);
        if(temp > maximum)maximum = temp;
        temp = fuzz_comp(pk1[idx2],pk2[idx1]);
        if(temp > maximum)maximum = temp;
    }
    result[idx1-7] = maximum;
}
for(idx1 = right_index;idx1 < right_index + lim3; idx1++)
{
    maximum = 0.0;
    for(idx2 = idx1 - indices[lim2];idx2 < idx1+indices[lim2];idx2++)
    {
        temp = fuzz_comp(pk1[idx1],pk2[idx2]);
        if(temp < maximum)maximum = temp;
        temp = fuzz_comp(pk1[idx2],pk2[idx1]);
        if(temp < maximum)maximum = temp;
    }
    result[idx1-7] = maximum;
}
fprintf(stderr,"Finished other side, accumulating.\n");
sum = 0.0;
/* copy result into cumresult for accumulation */
for(idx1 = 0; idx1 < PEAKS;idx1++)
{
    sum += result[idx1];
    cumresult[idx1] = result[idx1];
}
```

FUZZ_COM.C

```
    sum = sum/(double)(max(npeaks,npeaks2)-offset);
    /* compute the result vectors */
    for(idx1 = 7; idx1 < (max(npeaks,npeaks2))+7-offset;idx1++)
    {
    /*if(result[idx1] == 0.0)continue;*/
        if(idx1 > 0)
        cumresult[idx1-7] += cumresult[idx1-8];
        cumdindex[idx1-7] = cumresult[idx1]/(double)(idx1-6);
        fprintf(out,"%f , %f\n",result[idx1-7],cumdindex[idx1-7]);
    }
    fprintf(out,"%f",sum);
    exit(0);
}
```

501index.h

```
/*
 * Include file to give the scan number of the mass ratio
 * 501 peak, for each run. The first number is the number of
 * entries in the file, the remainder is an array of two element
 * structures. The first element is the run number (without the
 * "B"!), e.g. run 10B would be 10. The second number is the
 * index of the peak value for mass 501 for that run.
 */

const int NumEntries = 10;
struct
{
    int run;
    int index;

}entry[] =
    {
        {10,211},
        {12,207},
        {13,209},
        {14,208},
        {16,206},
        {17,215},
        {18,206},
        {19,216},
        {21,217},
        {23,219}
    };
```

501index.h

```
#include <stdio.h>

double
fuzz_comp(double aa, double bb)
{

    double temporary;

    /*if(aa == bb)return 1.0;*/

    /* Threshold is set to 0.3 for test runs 10b-23b.*/
    if(aa < 0.3 || bb < 0.3)return 0.0;

    else if(aa > bb && bb != 1.0)
    {
        temporary = 0.5*((bb/aa) +((1.0-aa)/(1.0 - bb)));
        return temporary;
    }else if(aa != 1.0)
    {
        temporary = 0.5*((aa/bb) + ((1.0 - bb)/(1.0 - aa)));
        return temporary;
    }else
        return 1.0;
}
```

What is claimed is:

1. A method for detecting the presence of *M. tuberculosis* in a sample, comprising the step of analyzing said sample for the presence of either or both of two characterizing compounds having m/e values of 484 and 486 and GC retention times relative to a $d_{37}$-octadecyl alcohol internal standard of about 1.022 and about 1.032, respectively, when derivatized with pentafluorobenzoyl chloride.

2. The method of claim 1, further comprising the step of detecting 2-eicosanol in said sample, wherein said m/e 486 compound has a GC-MS peak having a first peak area, wherein the ratio of said first peak area to a second peak area, said second peak area comprising said 2-eicosanol, is greater than one.

3. The method of claim 1, wherein said sample is sputum, alveolar washings or bronchial alveolar lavage.

4. The method of claim 1, wherein said characterizing compounds are fatty alcohols.

5. The method of claim 1, further comprising culturing said sample prior to said analyzing step.

6. The method of claim 1, wherein said analyzing step is GC-MS or MS-MS.

7. The method of claim 1, further comprising the steps of detecting a reference compound common to more than one species of mycobacteria and comparing the quantity of said reference compound to the quantity of said characterizing compound or compounds.

8. The method of claim 7, wherein said reference compound is 2-eicosanol, and wherein the quantity of at least one said characterizing compound is about equal to or greater than said reference compound if *M. tuberculosis* is present in said sample.

9. The method of claim 8, further comprising obtaining and comparing GC-MS peaks for said 2-eicosanol and said m/e 486 compound to determine the relative quantities thereof in said sample.

10. A method of identifying a microorganism present in a sample, said method comprising the steps of analyzing said sample by GC-MS to obtain a first set of GC-MS ion species data; and comparing said first set of GC-MS ion species data to a panel of GC/MS ion species data by a fuzzy matching process to generate fuzzy match integral data vectors, wherein said panel of GC/MS ion species data comprises data from known species of microorganisms.

11. The method of claim 10, further comprising for at least one of said known species of microorganism, identifying a GC-MS peak characteristic of said species and determining whether said characteristic peak is present in said sample.

12. The method of claim 10, further comprising the step of using an adjustable aggregation process simultaneously utilizing all of said ion species data to reduce said integral data vectors to aggregated scalar values using a vector dot product of a sorted list of the ion species data.

13. The method of claim 12, wherein said aggregation process is maximum entropy-ordered weighted averaging.

14. The method of claim 12, further comprising the step of using an ARG MAX to choose a proper index among said aggregated scalar values.

15. The method of claim 10, further comprising the step of using a threshold modified matching function is used to eliminate noise in said GC-MS ion species data.

16. The method of claim 10, wherein said microorganism is a mycobacterium.

* * * * *